US011123083B2

(12) United States Patent
Spickermann et al.

(10) Patent No.: US 11,123,083 B2
(45) Date of Patent: Sep. 21, 2021

(54) DEVICE AND METHOD FOR HEMOSTASIS AT THE PUNCTURE SITES OF PATIENTS' BLOOD VESSELS AS WELL AS AN EVALUATION UNIT HAVING A SENSOR

(71) Applicant: FRESENIUS MEDICAL CARE DEUTSCHLAND GMBH, Bad Homburg (DE)

(72) Inventors: Reiner Spickermann, Wasserlosen-Burghausen (DE); Pascal Kopperschmidt, Dittelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 273 days.

(21) Appl. No.: 15/753,748

(22) PCT Filed: Aug. 2, 2016

(86) PCT No.: PCT/EP2016/068431
§ 371 (c)(1),
(2) Date: Feb. 20, 2018

(87) PCT Pub. No.: WO2017/029111
PCT Pub. Date: Feb. 23, 2017

(65) Prior Publication Data
US 2018/0250018 A1    Sep. 6, 2018

(30) Foreign Application Priority Data
Aug. 17, 2015   (DE) .................... 10 2015 010 743.7

(51) Int. Cl.
*A61B 17/135*    (2006.01)
*A61M 1/14*    (2006.01)
(Continued)

(52) U.S. Cl.
CPC ...... *A61B 17/1355* (2013.01); *A61B 17/1322* (2013.01); *A61M 1/3653* (2013.01);
(Continued)

(58) Field of Classification Search
CPC ............. A61B 17/132; A61B 17/1322; A61B 17/1325; A61B 17/1355; A61B 2017/00199; A61M 1/14; A61M 1/3653
See application file for complete search history.

(56) References Cited

U.S. PATENT DOCUMENTS

2003/0236548 A1    12/2003 Hovanes et al.
2007/0032818 A1*   2/2007 McEwen ............ A61B 17/1322
                                                              606/202
(Continued)

FOREIGN PATENT DOCUMENTS

CN    202235549    5/2012
CN    104337559    2/2015
(Continued)

*Primary Examiner* — Katherine M Rodjom
(74) *Attorney, Agent, or Firm* — Jacobson Holman PLLC

(57) ABSTRACT

The invention relates to a device and a method for stopping bleeding at the puncture sites of vessels of patients undergoing an extracorporeal treatment, in particular dialysis. The device has a controller which controls the introduction of fluid into an expandable chamber arranged on a strip-shaped basic element and/or draining from the chamber. The invention also relates to an evaluation unit having at least one sensor for measuring the degree of filling of the chamber. Furthermore, the invention relates to a medical technical treatment unit as an arrangement of a hemodialysis machine and the device.

17 Claims, 5 Drawing Sheets

Figure 1A:
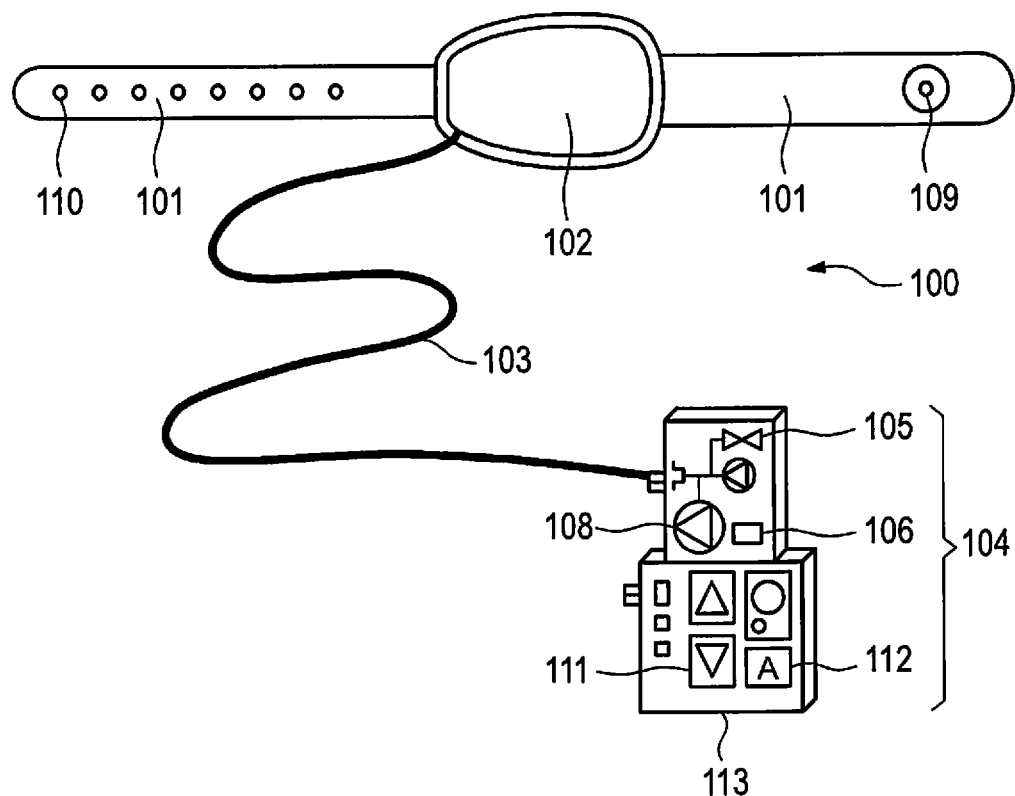

(51) Int. Cl.
*A61B 17/132* (2006.01)
*A61M 1/36* (2006.01)
*A61B 17/00* (2006.01)

(52) U.S. Cl.
CPC . *A61M 1/3655* (2013.01); *A61B 2017/00199* (2013.01); *A61M 1/14* (2013.01)

(56) References Cited

U.S. PATENT DOCUMENTS

| | | | | |
|---|---|---|---|---|
| 2013/0085524 | A1* | 4/2013 | Dahlberg | A61B 17/1325 606/202 |
| 2014/0031781 | A1* | 1/2014 | Razon-Domingo | A61F 13/56 604/385.03 |
| 2015/0018869 | A1* | 1/2015 | Benz | A61B 17/135 606/203 |
| 2015/0201948 | A1* | 7/2015 | Kornowski | A61B 5/0261 606/203 |

FOREIGN PATENT DOCUMENTS

| | | |
|---|---|---|
| DE | 29815375 | 7/1999 |
| EP | 0462088 | 12/1991 |
| EP | 1125554 | 8/2001 |
| EP | 1382306 | 1/2004 |
| WO | WO 98/46144 | 10/1998 |
| WO | WO 2011/090429 | 7/2011 |

* cited by examiner

DEVICE AND METHOD FOR HEMOSTASIS AT THE PUNCTURE SITES OF PATIENTS' BLOOD VESSELS AS WELL AS AN EVALUATION UNIT HAVING A SENSOR

The invention relates to a device, which makes it possible to stop the bleeding at the puncture sites of the blood vessels of patients undergoing an extracorporeal treatment, in particular dialysis, as well as a method for doing so. The invention also relates to an evaluation unit having at least one sensor and a medical technical treatment unit which represents an arrangement of a hemodialysis machine and this device.

It has long been known that devices which serve to compress vessels, so that blood flow in these vessels can be reduced or interrupted completely, can be used to control bleeding or even complete hemostasis thereof. For example, compression belts for controlling bleeding are known from the traditions of ancient Greek scholars as well as from the Roman Empire. Military surgeons have used compression belts to control bleeding in amputations. In the year 1718, the French surgeon Louis Petit developed a mechanical instrument using a tension screw, which he called a tourniquet, to care for very severe bleeding. Compression tubing made of a flexible material can be traced back to an invention by Johann von Esmarch in the year 1873, which offers the advantage that it does not have any mechanical parts that can become loosened.

Modern tourniquets are operated either pneumatically or mechanically and resemble a blood pressure cuff in appearance and function. Mechanical tourniquets function by shortening a belt by rotation. However, they may result in injury to the tissue and nerves. Another risk lies in the formation of blood clots. To achieve the required pressure, air is pumped into a balloon, which is incorporated into a cuff in the case of pneumatic tourniquets. This procedure entails less risk of injury.

Devices for compression of blood vessels are used for various purposes in medicine, for example, for compression of superficial veins in withdrawing blood, in phlebography or in surgery on extremities, to make it possible to perform an operation in a region of minimal bleeding. Devices of this type are also used to stop the bleeding at the puncture site after the end of the treatment and after removal of the hollow needle from the blood vessel using extracorporeal methods, in which blood is taken from a patient's blood vessel by means of a hollow needle through the skin during the treatment, then is directed into an extracorporeal circulation and returned back to the patient after the treatment.

To ensure adequate blood flow during a treatment by an extracorporeal method, hollow needles of a larger diameter are used to open the blood vessels, so that a substantial permanent pressure is required to close the puncture site again after removing the needle. Furthermore, anticoagulants such as heparin are often used in extracorporeal procedures, so that the secondary bleeding time is lengthened.

How easily and within how much time the bleeding at the puncture sites can be stopped after the hollow needles have been removed may vary greatly from one patient to the next and depends on a variety of factors, such as, for example, the properties of the vascular wall, the viscosity of the blood, the patient's blood pressure and/or age. Another important factor is whether the punctured vessel is an artery or a vein, because arterial bleeding is more difficult to stop. The type of puncture (for example, rope ladder puncture, buttonhole puncture, area puncture, etc.) and the patient's behavior after removal of the hollow needles have a considerable influence on the secondary bleeding time, which is prolonged if the patient moves a lot, for example, and thereby increases the blood pressure and the pressure on the puncture site.

Therefore, it often happens that a treatment station is not freed up because a patient's bleeding has not yet been stopped.

Hygienic problems can also occur due to a prolonged secondary bleeding time.

If a constant pressure is applied to the puncture sites of access by the nursing staff, this also results in a very time-consuming and expensive procedure.

It is very uncomfortable for the patient if it is left up to the patient to press on the puncture site, and this can result in inadequate closure of the vessel and thus renewed bleeding. If the patient has already departed from the treatment area, this can lead to health problems in the patient and to organizational difficulties in the treatment unit.

It is also difficult when pressing on a puncture site to maintain a constant compressive force continuously. Furthermore, it is difficult to apply a force which takes into account the adapted need for pressure to prevent secondary bleeding.

Therefore, several devices which ensure pressing on a vessel by mechanical means have already been developed.

Thus, the document EP 0 462 088 describes a device for pressing on the femoral artery, where the device consists of a belt and a base plate having means for establishing a reduced pressure, wherein the base plate and the means for establishing a reduced pressure are manufactured of a transparent material at least in part.

EP 1 382 306 proposes a hemostasis device, which includes a flexible belt with a plate curved toward the inside. The latter has a balloon into which fluid can be introduced for inflating it and also has a smaller pressing element, which is filled with a second fluid against this balloon presses.

EP 1 125 554 describes a venous congestion device having a pressure tube cuff, a pressure source and a pressure-adjusting aid. The compressive force is adjusted so that pressure is applied to a vein, but the flow cross section of the artery is at least partially maintained. The pressure value is either determined in advance by experiments for different patients or is calculated individually by means of a blood pressure measurement.

DE 298 15 375 relates to a compression belt for closing the puncture site of vessels in dialysis patients. The belt has an elastic material, which faces the puncture site with a plug which is adapted to the size of the puncture site and has the effect of applying a pressure to it.

WO 2011/090429 describes a compression unit having an inflatable balloon for applying pressure to a puncture site in a patient's artery.

Hemodialysis is the most common extracorporeal procedure. In this procedure blood is taken from the patient either through the same hollow needle or through a second hollow needle which is also inserted into a blood-carrying vessel and then the blood is returned to the patient.

Despite this need, no suitable hemostasis means, which can be used on dialysis patients in particular, have yet been developed. An additional problem that occurs with dialysis patients is that the puncture site must be punctured regularly and at short intervals. To avoid an excessive burden on the puncture site, an access in the form of a vascular design, for example, a fistula or a shunt, is usually created surgically. Fistulas and shunts are regions of a high blood flow, so that a high pressure must be applied to stop the secondary bleeding. However, complete blockage of the blood flow should be avoided, but that is problematical to achieve. Some health authorities have even advised explicitly against the use of such cuffs because they are associated with an increased health risk for the patient. For example, reference is made here to the BC Renal Agency "Vascular Access Guidelines" of 12 Oct. 2011, which contains this statement: "Clotting device such as a tourniquet or strap (not recommended)." Bleeding in dialysis patients is therefore usually still treated as it was before by applying pressure manually to a piece of textile, e.g., gauze, on the puncture site.

The object of the invention is therefore to make available a device and a method, which will make it possible to permanently and safely stop the bleeding at the puncture sites of the vessels of patients undergoing an extracorporeal treatment, in particular dialysis, in the shortest possible period of time, and thus avoid the disadvantages of the previous systems and procedures.

Another object of the invention is easy usability, i.e., convenient and simple application of the device.

In addition, the device should be simple and inexpensive to manufacture.

This object is achieved according to the invention by the features described below of the invention device for stopping bleeding. The invention device for stopping bleeding has a strip-shaped basic element with closure means, at least one first expandable chamber on the strip-shaped basic element, a fluid supply device, which is arranged in such a way that the fluid can be introduced through it into the at least one first chamber and/or can be discharged from it, a conveyance unit for introducing a fluid into the at least one first chamber, a valve for draining off the fluid out of the at least one first chamber and a control unit for controlling the conveyance unit and/or the valve, wherein the control unit has a memory, in which at least one profile is stored for controlled introduction of the fluid into the at least one first chamber and/or discharge of the fluid out of the at least one first chamber.

Advantageous embodiments of the invention device for stopping bleeding are described below.

This object is also achieved according to a method having the features of the invention device for stopping bleeding which method comprises the following steps:

Applying the device to the chamber over the puncture site,
determining a profile,
introducing a fluid into the chamber,
discharging the fluid,
removing the device.

The invention includes an evaluation unit for the device for stopping bleeding according to the invention, having at least one sensor which measures the filling level of the at least one first chamber.

The invention includes a medical technical treatment unit having a device for stopping bleeding according to the invention and a blood treatment device, in particular a hemodialysis machine which is equipped to communicate with the data transmission device.

The device according to the invention has a strip-shaped basic element with closure means and at least one first expandable chamber on the strip-shaped basic element.

The strip-shaped basic element preferably is made of a material that is preferably flexible or elastic and is easy to clean, such as a fabric, rubber, plastic or the like. For example, plastic is a material that is relatively inexpensive and is easy to work on and allows the basic element to be used as a disposable item.

The strip-shaped basic element may have a closure means by means of which it can preferably be shaped into a ring or a partial ring and can be fastened by extending around a patient's extremity. The closure means may be made of plastic. Closure means that may be considered include, for example, means that cannot be positioned continuously such as snaps, pushbuttons or the like. This permits better reproducibility without the need for regulating the filling level in the one or more chambers. However, continuously adjustable closure means such as Velcro-type closures or ratcheted closures are also conceivable.

In the ring-shaped arrangement, the basic element may be designed to be stiffer on the outside than on the inside in at least one part of the region of the at least one first chamber. Due to these reinforced regions, the expansion of the chamber region can be directed more inwardly than outwardly.

For correct positioning of the chamber over the puncture site, the at least one first chamber is at least partially transparent.

The chamber is made of a flexible, preferably elastic material so that it can expand when the fluid is supplied, i.e., it is expandable. Since the volume of the chamber is variable, the force with which pressure is applied to the puncture site can be adjusted through the choice of a suitable pressure.

The dimensions of the chamber in the longitudinal direction are smaller than the dimension of the basic element, but may preferably be less than one half the dimensions of the basic element.

The chamber can be connected by a fluid supply device, which may be a tubing, for example, to a conveyor unit, which has a pump, for example, which may be a cartridge or a syringe under pressure, for insertion of a fluid into the chamber.

The chamber may also be formed by two interconnected flat regions of different sizes. The volume of the chamber can therefore be increased when the fluid is introduced. The two flat regions forming the first chamber may be stiff to differing extents. Therefore, expansion can take place in a targeted manner in one direction with inflation.

A gas is preferably used as the fluid but use of a liquid is also conceivable.

For draining the fluid out, the device also has a valve which is connected to the fluid supply device, so that fluid in the at least one first chamber can be drained out. The conveyor device can also function as a valve by actively conveying fluid out of the chamber.

The device also has a controller, which controls the conveyor unit and/or the valve and is equipped with a memory. The memory contains at least one profile, according to which the fluid can be introduced into the at least one first chamber or drained out of it in a defined manner.

The profile by which fluid is introduced into the chamber or drained out of the chamber can be characterized by a predefined maximum pressure. The profile can be characterized by various curves over time, in which a valve is opened and/or the degree of opening of a valve is changed or the conveyor unit is operated, or the profile may have a linear, step-shaped or exponential curve. Furthermore, it is conceivable for the profile to depend on certain measurement equipment that analyzes the extent of the bleeding.

The profile may also be characterized in that the degree of filling in the first chamber is increased temporarily when the conveyor unit is controlled according to the profile.

A plurality of profiles can be stored in a memory, for example, at least two profiles, which differ in that the degree of filling can be reduced at different rates.

Storage of profiles is advisable in particular when the same patient visits one facility rather frequently for extracorporeal treatment, as in the case of dialysis, for example, because then different profile parameters are known and particular details of the treatment can be taken into account.

The device according to the invention may have an input device, with which the at least one profile can be selected. The input device may include operating elements for selection of the profile. Furthermore, it may also have a display for selection of the profile. The controller and the input device are preferably integrated into a common portable housing.

The device according to the invention may also have at least one sensor for measuring the degree of filling in the at least one first chamber and the conveyor unit and/or the valve may be controllable by the controller on the basis of the measured value transmitted by the sensor. This can be achieved by means of a processor arranged in the controller. By measuring an actual value of the degree of filling of the first chamber, the actual value can be influenced by the controller. The sensor may be arranged on the first chamber or integrated into the feed device or the controller.

If gas is used as a fluid, the sensor may be a pressure sensor and the measured value may be a pressure value. In the case of hemodialysis patients, greater pressure values are not necessary; for example, pressures between 50 mmHg and 150 mmHg may be sufficient, so that small dimensions of the conveyor unit are possible.

The device according to the invention is not limited to the actual basic element that is to be brought to the patient but instead may include other elements, such as, for example, the controller, the fluid feed device or the conveyor unit, which are connected to the basic element.

The controller may be a device that can be held in the hand so that the patient enjoys increased mobility and can leave the treatment facility, for example. Whereas the basic element may be designed as a disposable item, the controller may be reusable. To this end the controller and the basic element may also be designed to be separable.

At least one or more of the components from the group of components consisting of sensor, conveyor device or input device may be integrated into the handheld device.

It is also conceivable for the device according to the invention to have a second expandable chamber in the basic element, so that positioning of the cuff is possible even with two puncture sites (withdrawal site and return site for the blood) and the pressure can be applied to two puncture sites in an optimized manner. When there is only one large chamber, the pressure may be the greatest in the region between the two puncture sites.

The second chamber may have the same design as the first chamber. Both the first chamber and the second chamber may be manufactured at least partially or completely of a transparent material.

The two chambers may be arranged on an axis perpendicular to the strip-shaped basic element. This arrangement corresponds to the relative orientation of the two puncture sites in a dialysis patient.

A gas-permeable channel may be provided between the first chamber and the second chamber. The basic element may have a varying stiffness in the region of the chambers, so that the channel can be shaped when filling the first and second chambers. The channel may have a reduced width and/or a reduced height in comparison with the first chamber and the second chamber. The channel permits filling and emptying of the first chamber and of the second chamber through just one feed device. One of the chambers has at least one feed site and one outlet site for a fluid.

The first chamber and the second chamber may also be arranged so they are isolated from one another, and each may have its own feed site and/or drain site for a fluid.

The device according to the invention may also have a second conveyor unit which is arranged in such a way that a fluid from the second chamber may be discharged through the feed mechanism.

At least one profile for controlled discharge of the medium out of the second chamber may be stored in the memory. The profile for discharge of gas from the first chamber may be different from the profile for discharge of gas out of the second chamber.

The controller may have a data transmission device and a processor, wherein the processor is suitable for determining a profile by means of the data transmitted through the data transmission device. The suitability can be achieved, for example, by the fact that the data transmission device is an interface from the group consisting of a manual input device, a wireless or hardwired communication interface. The data may be data from the group consisting of the patient identification, blood viscosity, hematocrit, fistula pressure and/or shunt pressure, a profile-specific code, dialysis treatment parameters, the ACT (activated clotting time) or anticoagulation regimen parameters.

The blood viscosity and hematocrit of the blood can be determined by means of an ultrasonic or optical measurement device such as those used in hemodialysis machines, during a dialysis treatment.

The memory can store profiles for various patients or patient groups. By transmission of a patient identification or a profile-specific code, the controller can be programmed to select a corresponding profile. Blood-specific values can be transmitted for selection of the profile by the controller. A blood-specific value may be, for example, the blood viscosity or the hematocrit.

When a profile is mentioned in this description, it may be the profile for the first chamber and/or for the second chamber.

The processor in the control device can also carry out instructions by means of a program stored in the memory, so that the processor controls the conveyor device and/or the valve in accordance with the profile.

It is conceivable that the degree of filling of the chamber is measured by at least one sensor and the measured value is detected by an evaluation unit for correction of the profiles. The minimum pressure which is still sufficient for stopping the bleeding can be discovered in this way.

However, the sensor may also serve to measure various other values such as, for example, the temperature, humidity, etc., and thus to identify inadequate hemostasis. On the basis of the measured values, a separate profile can be created for each individual situation.

The device according to the invention can be integrated into a system for stopping bleeding at a puncture site of a hemodialysis patient, wherein the device is equipped to communicate with a blood treatment device, in particular a hemodialysis device, over the data transmission device. To do so, the blood treatment machine may also have a data transmission device. The data transmission device may be, for example, a LAN, a WLAN, a WiFi, a Bluetooth or an RFID interface.

Exemplary embodiments are explained in greater detail below with reference to the drawings.

Figure 1B:
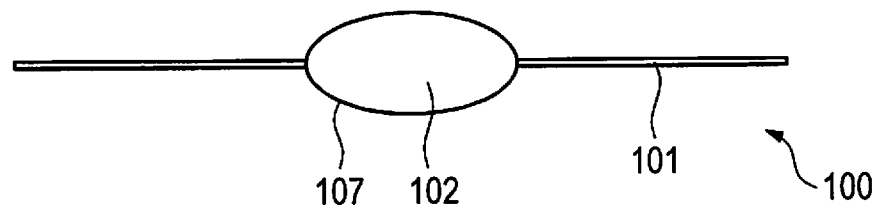
Figure 2:
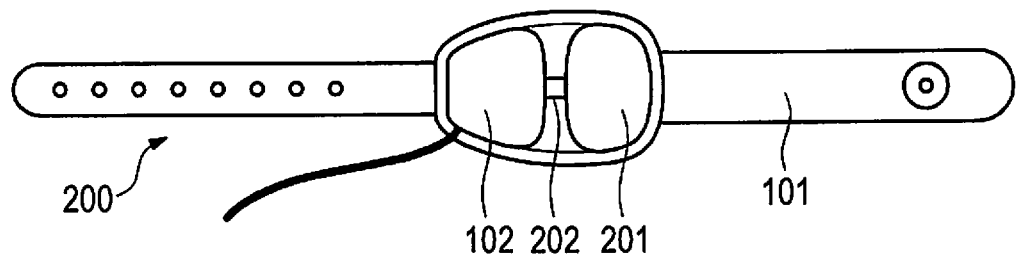
Figure 3:
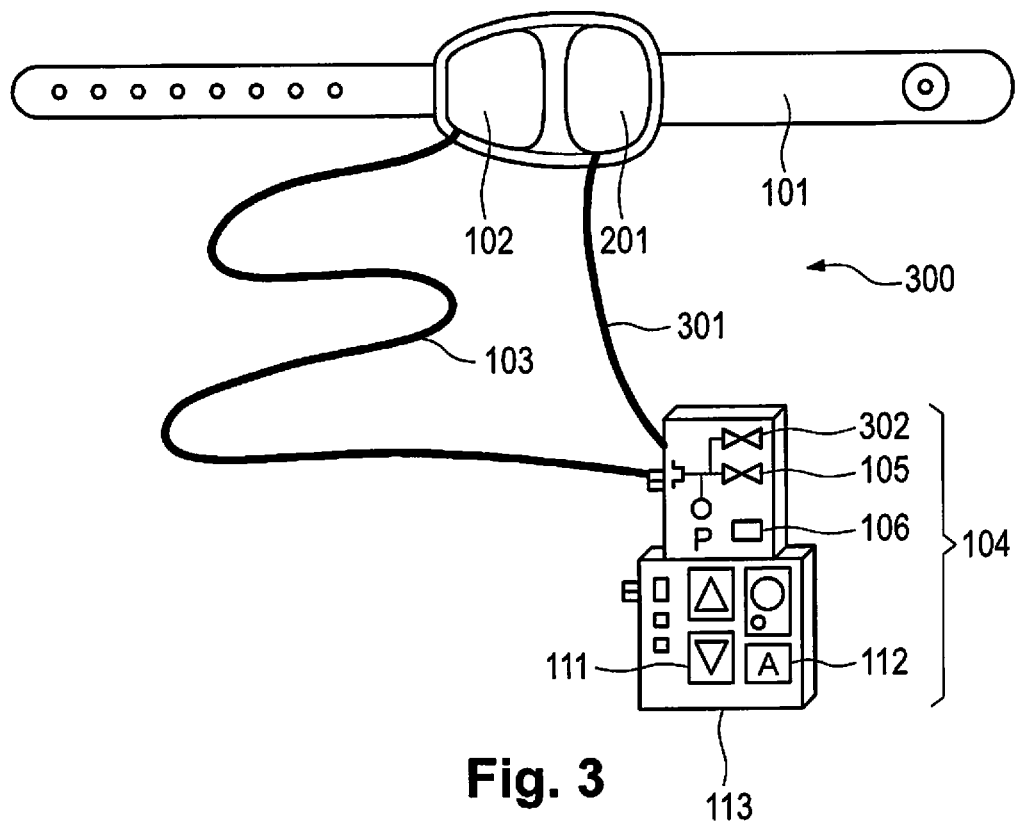
Figure 4:
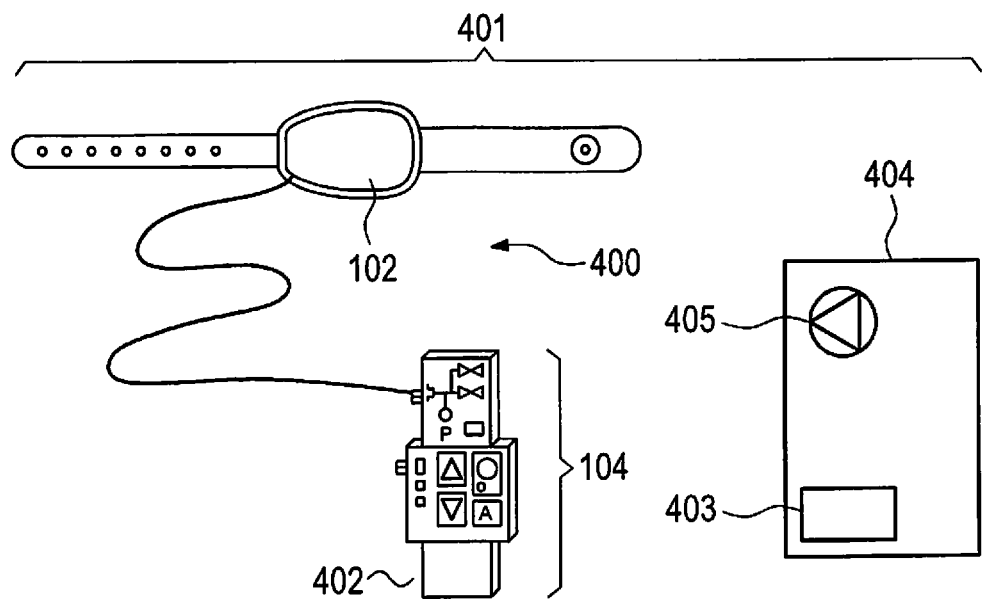
Figure 5:
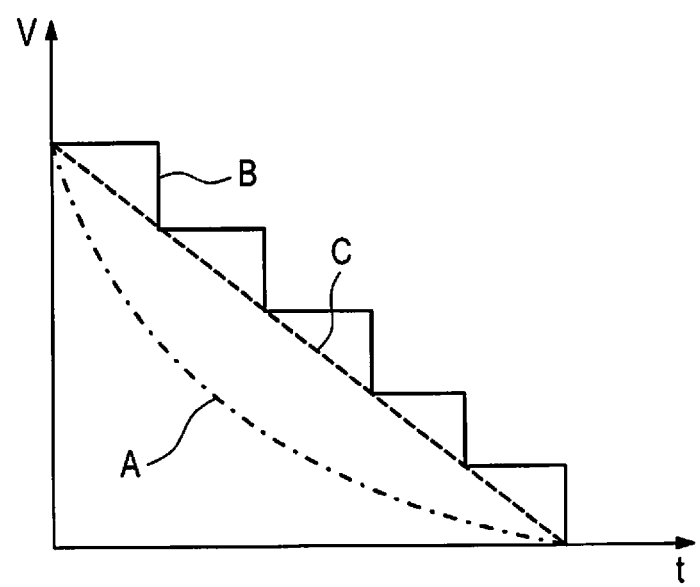
Figure 6:
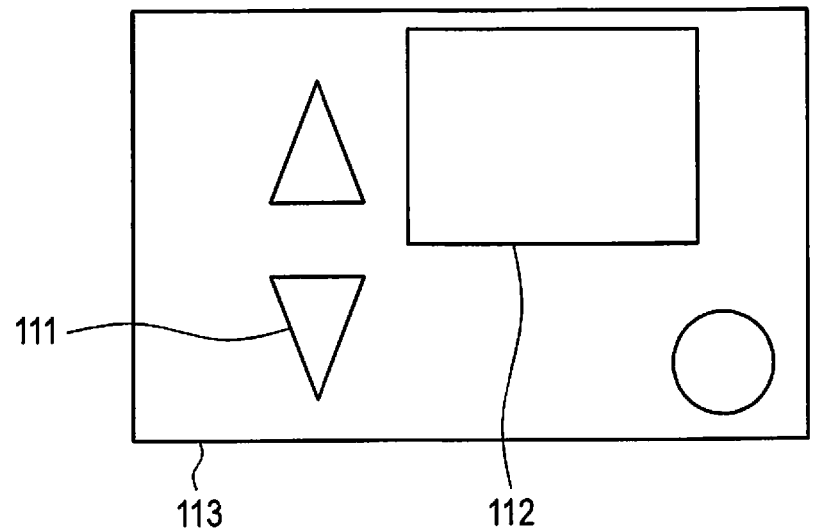
Figure 7:
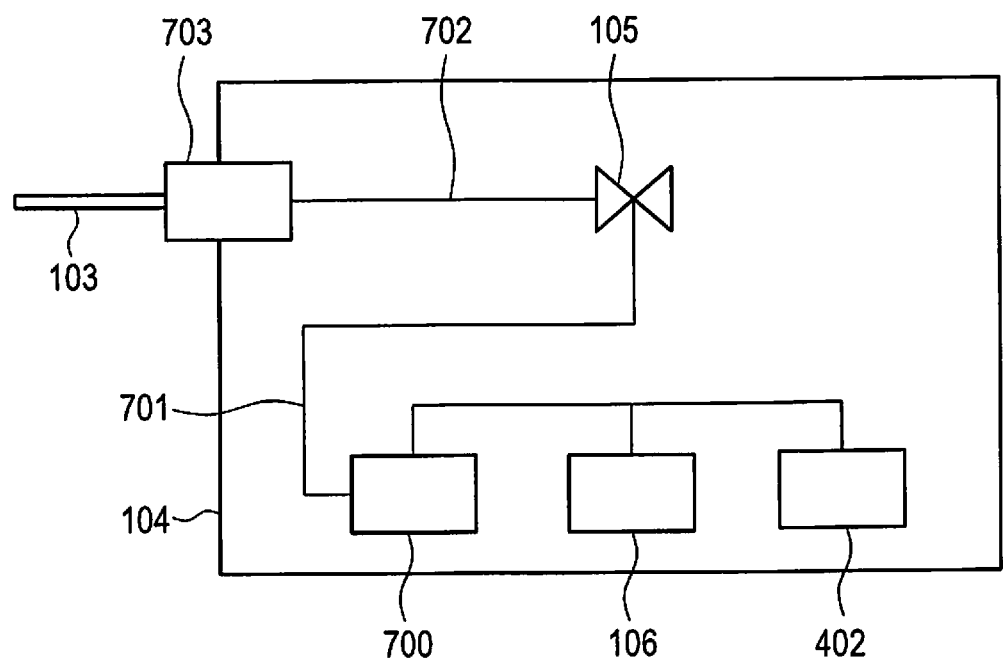
Figure 8:
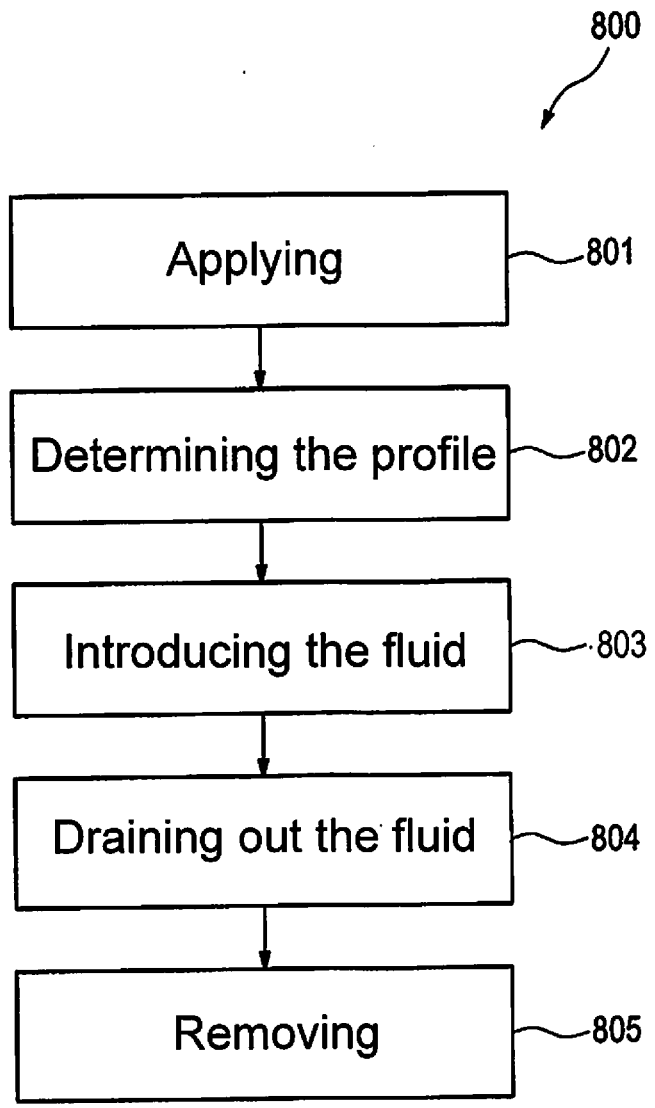

They show:

FIG. 1a: an embodiment of the device according to the invention with a chamber, in a view from above;

FIG. 1b: an embodiment of the device according to the invention with a filled chamber in a longitudinal section;

FIG. 2: another embodiment of the device according to the invention with two chambers connected to one another by a channel 202 in a view from above;

FIG. 3: another embodiment of the device according to the invention with two chambers insulated from one another in a view from above;

FIG. 4: a medical technical treatment unit with the device according to the invention and an extracorporeal blood treatment machine;

FIG. 5: embodiments for profiles for draining fluid from at least one of the chambers;

FIG. 6: an embodiment of the controller with a display and operating elements;

FIG. 7: an embodiment of the controller according to FIG. 6 with individual components;

FIG. 8: a method for stopping bleeding using the device according to the invention;

Corresponding features in the figures are labeled with the same reference numbers.

FIG. 1a shows the device 100 according to the invention in an inactive state. The device 100 has a strip-shaped basic element 101 with an expandable chamber 102 as well as connecting means, a pushbutton 109 here, for example, and the respective recesses 110. By means of this connecting device, the device 100 can be fastened in the form of a ring around an extremity, preferably one of the patient's arms.

A fluid supply device 103, through which a fluid can be introduced into the chamber when using the device 100, opens into the expandable chamber 102.

A conveyer unit 108 conveys fluid through the fluid supply device 103 into the chamber 102. The conveyer unit 108 may be a pump, for example.

The controller 104 has, in addition to the input device 113, a memory 106, in which at least one profile is stored, with which the degree of filling of the chamber 102 can be reduced when this profile is executed. The input device 113 may have operating elements 111 and a display 112. A profile can be selected by means of the operating elements 111 and the display 112 can display the profile or a plurality of profiles. The profile can be displayed as a graph, as a characteristic number or as a description and stored in the memory accordingly. The display 112 can display the remaining time until the pressure in the expandable chamber 102 has dissipated or a predetermined amount of time has elapsed. The operating elements 111 and/or the display 112 may be provided in the controller of each embodiment as described.

The valve 105 for draining the fluid out of the chamber 102 may be a pump, for example. The conveyer unit 108 and the controller 104 may cooperate, so that when using the device 100 according to the invention, first the degree of filling in the chamber 102 is increased, so that the chamber 102 expands and exerts a pressure on the puncture site. Then the controller 104, in cooperation with the valve 105, can reduce the degree of filling of the chamber 102 and thus the pressure on the puncture site in accordance with a predetermined profile.

FIG. 1b shows the device 100 according to the invention in the active state. The strip-shaped basic element 101 may be made of plastic, and the chamber 102 may be formed from two interconnected plastic layers 107. The fluid in the chamber 102 can be drained through the fluid feed device 103 by means of the controller 104 and a valve 105 that can be controlled by the controller 104.

FIG. 2 shows another embodiment of the device 200 according to the invention having a first expandable chamber 102 and a second chamber 201. The device 200 may have all the features of the device 100, as described with regard to FIG. 1. The two chambers 102 and 201 may be connected by a channel 202. Fluid can be introduced into and/or drained out of both chambers at the same time through this channel. When using the device 200 according to this additional embodiment, bleeding at two puncture sites can be stopped at the same time.

FIG. 3 shows another embodiment of the device 300 according to the invention. The device 300 has a first expandable chamber 102 and a second expandable chamber 201. The device 300 may have all the features of the device 200 as described with regard to FIG. 2. However, in this embodiment, the chambers 102 and 201 are isolated from one another. The controller 104 of the device 300 as shown in FIG. 3 can supply fluid into the second chamber 201 through another fluid supply device 301 in a controlled manner or can drain fluid out through another valve 302. The fluid supply device 301 and/or the valve 302 may be the same through which the fluid can be supplied to and/or drained from the first chamber.

When using the device 300 according to this additional embodiment, the pressure in the first chamber 102 can be reduced with a different profile than that from the second chamber 301.

FIG. 4 shows a medical technical treatment unit 401 according to the invention. The system has the device 400 according to one of the embodiments described and has an extracorporeal blood treatment machine 404, for example, a hemodialysis machine here. The controller 104 of the device 400 has a first data transmission device 402 and the blood treatment device 404 has a second data transmission device 403. Data can be transmitted from the blood treatment device 404 to the device 400 by means of the data transmission devices 402 and 403. The transmitted data can be used by the controller 104 for choosing or selecting a profile. The chamber 102 can also be filled by means of the conveyor device 405, which is situated in the blood treatment device 404.

FIG. 5 shows as an example three profiles such as those that can be stored in the memory 106 of the controller 104. These profiles illustrate the reduction in the degree of filling of the chamber 102 over time, where the curve of the profile may be exponential (A), step-shaped (B) or linear (C).

FIG. 6 shows one embodiment of the controller 104. The controller 104 has a display 112 and operating elements 111. A profile can be selected by means of the operating elements 111. A certain degree of filling of the chamber 102 is also adjustable by means of the operating elements 111 by the fact that the valve 105 can be controlled, optionally together with the conveyor unit 108, for draining and/or introducing fluid. The degree of filling of the chamber 102 can be measured with a sensor.

FIG. 7 shows one embodiment of the controller 104 with individual components. The controller 104 has a first data transmission device 402, a processor 700, a memory 106 and a valve 105. A communication line 701 is used for data transmission. The valve 105 may be arranged in a fluid line system 702, wherein the fluid line system 702 is suitable for connecting to the fluid feed device 103. The controller 104 may have an access 703 for connecting the fluid feed device 103 to the controller 104. When using a device having more than one chamber and a plurality of fluid feed devices, a plurality of accesses to the fluid line system may be provided.

FIG. 8 illustrates method 800 for stopping the bleeding at a puncture site on a patient's blood vessel. This method includes the steps: application 801 of the device with the chamber over the puncture site, wherein the device is placed around an extremity, preferably the patient's arm, determining 802 a profile according to which the pressure in the chamber is to be reduced, introducing a fluid 803 into the chamber up to a predetermined degree of filling, draining 804 the fluid according to the profile, removing 805 the device from the extremity, preferably from the patient's arm. The step of introducing the fluid 803 may take place before the step of applying 801 or determining 802. This has the advantage that it can take place independently of the patient. The degree of filling can then be adjusted by the closure device, for example. The step of determination 802 of the profile may include the step of data transmission 805 from an extracorporeal blood treatment device, wherein data transmitted in the step of data transmission 805 may be used for determination 802 of the profile. The method 800 may be carried out with any device according to the invention.

REFERENCE LIST 100 device
101 strip-shaped basic element
102 first expandable chamber
103 fluid feed device
104 controller
105 valve
106 memory
107 plastic layer
108 conveyor unit
109 pushbutton
110 recesses
111 operating elements
112 display
113 input device
200 alternative embodiment of the invention
201 second expandable chamber
202 channel
300 alternative embodiment of the invention
301 second fluid feed device
302 second valve
400 alternative embodiment of the invention
401 medical technical treatment unit
402 first data transmission device
403 second data transmission device
404 blood treatment machine
405 conveyor device
700 processor
701 communication line
702 fluid line system
703 access for connecting the fluid feed device
800 method for stopping bleeding
801 application
802 determining profile
803 introducing the fluid
804 draining the fluid
805 removal
A profile: exponential curve
B profile: step-shaped curve
C profile: linear curve

The invention claimed is:

1. A medical technical treatment unit comprising
   a) a device for stopping bleeding on at least one puncture site of a blood vessel of a patient who has undergone an extracorporeal treatment, in particular dialysis, comprising
      a strip-shaped basic element flexible along its entire length with closure means able to close the curvable basic element in the shape of a ring,
      at least one first expandable, at least partially flexible chamber directly on the strip-shaped basic element,
      a fluid feed device, which is arranged so that the fluid can be introduced through it into the at least one first expandable chamber and/or can be drained from it,
      a conveyor unit for introducing a fluid into the at least one first chamber,
      a valve for draining the fluid out of the at least one first chamber, and
      a controller for controlling the conveyor unit and/or the valve, wherein the controller has a memory storing at least one profile for controlled introduction of the fluid into the at least one first chamber and/or draining of the fluid out of said chamber, and wherein the controller has a data transmission device and a processor suitable for determining the profile on the basis of data transmitted by the data transmission device, and
   b) an extracorporeal blood treatment device equipped to communicate with the data transmission device.

2. The treatment unit according to claim 1, characterized in that the basic element is designed to be more rigid in at least one part of the region of the first chamber on one exterior side than on an interior side when the strip-shaped basic element is curved in the form of a ring.

3. The treatment unit according to claim 1, characterized in that the at least one first chamber is at least partially transparent.

4. The treatment unit according to claim 1, wherein the dimensions of the chamber are smaller in the longitudinal direction than the dimensions of the basic element.

5. The treatment unit according to claim 1, characterized in that the device for stopping bleeding includes an input device, with which the at least one profile can be selected.

6. The treatment unit according to claim 1, characterized in that the device for stopping bleeding includes a sensor for measuring the degree of filling of the at least one first chamber.

7. The treatment unit according to claim 6, characterized in that the conveyor unit and/or the valve can be controlled on the basis of the measured degree of filling.

8. The treatment unit according to claim 1, characterized in that the conveyor unit creates a pressure of 50 mmHg to 150 mmHg.

9. The treatment unit according to claim 1, characterized in that a second chamber is present on the basic element at a distance from the first chamber, wherein the first and the second chambers are connected via a fluid-permeable channel, and one of the chambers has at least one feed location and/or discharge location for a fluid.

10. The treatment unit according to claim 1, characterized in that a second chamber is present on the basic element at a distance from the first chamber, wherein the first and second chambers are arranged in isolation from one another and each has at least one feed location and/or drain location for a fluid.

11. The treatment unit according to claim 1, characterized in that the data transmission device is an interface of the group consisting of a wireless communication interface and a hardwired communication interface.

12. The treatment unit according to claim 1, characterized in that the data are selected from the group consisting of patient identification, blood viscosity, hematocrit, fistula pressure, shunt pressure, fistula pressure and shunt pressure, profile-specific code, dialysis treatment parameters, ACT (activated clotting time), and anticoagulation regimen parameters.

13. A method for stopping bleeding of at least one puncture site of a blood vessel of a patient undergoing an extracorporeal treatment, in particular dialysis, comprising the steps:
   applying the device for stopping bleeding of the treatment unit according to claim 1 with the chamber over the puncture site,
   determining a profile,
   introducing a fluid into the chamber,
   draining the fluid,
   removing the device for stopping bleeding.

14. An evaluation unit for a treatment unit according to claim 1, having at least one sensor which measures the degree of filling of the at least one first expandable chamber.

15. The treatment unit according to claim 1, characterized in that the at least one first chamber is elastic.

16. The treatment unit according to claim 1, wherein the dimensions of the chamber are less than one-half of the dimensions of the basic element.

17. The evaluation treatment unit according to claim 1, characterized in that the extracorporeal blood treatment device is a hemodialysis machine.

* * * * *